United States Patent [19]
Bentley et al.

[11] Patent Number: 5,500,735
[45] Date of Patent: Mar. 19, 1996

[54] METHOD AND APPARATUS FOR ON-LINE MEASUREMENT OF PULP FIBER SURFACE DEVELOPMENT

[75] Inventors: Roger G. Bentley, Pierrefonds; R. Keith Hamilton; J. Stewart Jack, both of Pointe Claire; Robert L. Barron, Surrey, all of Canada

[73] Assignee: Pulp and Paper Research Institute of Canada, Pointe Claire, Canada

[21] Appl. No.: 276,801

[22] Filed: Jul. 18, 1994

[51] Int. Cl.$^6$ .......................... G01N 21/21; G01N 21/05
[52] U.S. Cl. ............................................. 356/364; 356/246
[58] Field of Search ..................................... 356/364, 365, 356/366, 367, 246

[56] References Cited

U.S. PATENT DOCUMENTS 3,283,644  11/1962  Saltzman .

(List continued on next page.)

FOREIGN PATENT DOCUMENTS 938128  12/1973  Canada .

(List continued on next page.)

OTHER PUBLICATIONS

"Bridge & Hamer, Paper Tech Ind 18(12)" 37 (1977) (Feb. 1977).
Casey, (Pulp and Paper, 3rd Ed. vol. 2, p. 839 (1980)).
Clark (Tappi 45(8): 628 (1962) (Aug. 1962).
Zellstoff Papier 32, No. 4: 154:157 (Jul./Aug. 1983) Comparative Examination of Different Methods for Determining Specific Surface of Pulp Fibers in Suspension.
Forgacs (PPMC 64(C): T89 (1963) The Characterization of Mechanical Pulps.
Hamer, (Paper Tech 15(5): 263(1974) The Characterization of Stock Properties (Oct. 1974).
Ingmanson (Tappi 35(10): 439(1952) An Investigation of the Mechanism of Water Removal from Pulp Slurries (Oct. 1952).
Mason, (Tappi 33(8): 403(1950) The Specific Surface of Fibers–Its Measurement and Application (Aug. 1950).
Meyn et al. (J. Institute of Measurement & Control) 1(9): T165 (1968) An Instrument for the Continuous Measurement of Low Fibre Concentration etc. . . .
Olander, Kerstin (Tappi 81(1991) Specific Surface Area–An Important Property of Mechanical Pulps.
Parker and Mih, (Tappi 47 (5): 254(1964)–A New Method for Sectioning and Analyzing Paper in the Transverse Direction (May 1964).
Robertson and Mason, (PPMC 50(13): 1(1949) Specific surface of cellulose fibres by the liquid permeability method (Dec. 1949).
Shimuzu, Usuda and Kadoya (Japan Tappi 35(7): 609(1981) Evaluation of Fibrillation of Paper Making Fibers in Suspension by Optical Method.
Silvy and Pascal, (ATIP (22): 205(1968) L;observation en continu des suspensions fibreuses, methode pratique de controle de fabrication.

Primary Examiner—Richard A. Rosenberger
Attorney, Agent, or Firm—Swabey Ogilvy Renault

[57] ABSTRACT

A method and apparatus for monitoring the fiber surface development of pulps due to the refining or beating of mechanical or chemical pulps; an optical cell, fabricated with light-transparent windows, permits an incident collimated beam of light to pass through pulp stock flowing through the cell. The beam is transmitted through a polarizing filter prior to entering the cell, and through a second, crossed, polarizing filter, on exiting from the cell. The exit beam converges onto a photodetector. A gradual variation in the mass of fibers of the pulp stock is established over a predetermined range and this produces a change in the intensity of the transmitted light. As the light intensity changes, it passes through a maximum value; this is accompanied by a similar change in the photodetector electrical output signal. The photodetector signal is fed into a signal processor which generates an output corresponding to the maximum photodetector output value, and this represents an index of the degree of fiber surface development.

17 Claims, 5 Drawing Sheets

U.S. PATENT DOCUMENTS

| | | | |
|---|---|---|---|
| 3,518,003 | 6/1970 | Meyn | 356/367 |
| 3,724,957 | 4/1973 | Tamate | 356/367 |
| 3,802,964 | 4/1974 | Forgacs . | |
| 4,135,389 | 1/1979 | Karnis et al. . | |
| 4,159,639 | 7/1979 | Simms et al. . | |
| 4,171,916 | 10/1979 | Simms et al. | 356/366 |
| 4,276,119 | 6/1981 | Karnis et al. . | |
| 4,441,960 | 4/1984 | Karnis et al. . | |
| 4,529,309 | 7/1985 | Pettersson et al. . | |
| 4,676,641 | 6/1987 | Bott . | |
| 4,971,441 | 11/1990 | Damlin et al. | 356/246 |

FOREIGN PATENT DOCUMENTS

| | | |
|---|---|---|
| 1123626 | 5/1982 | Canada . |
| 3105752 | 2/1982 | Germany . |
| 218463 | 2/1985 | Germany . |
| 7706320 | 12/1978 | Sweden . |
| 1075123 | 2/1984 | U.S.S.R. . |

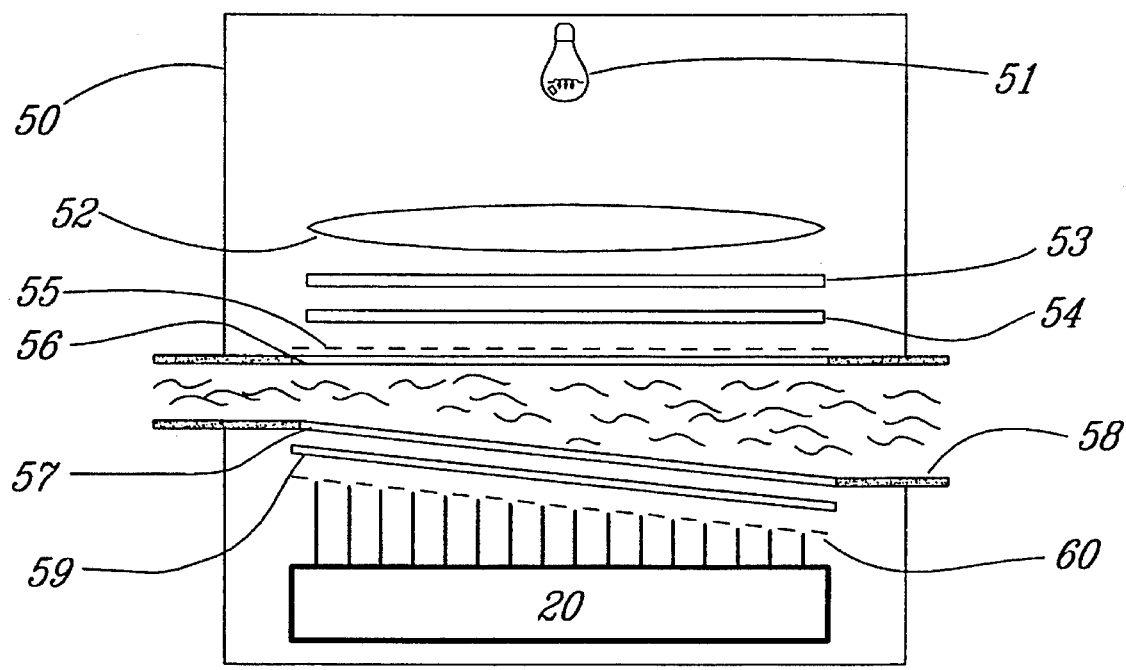
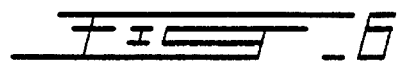
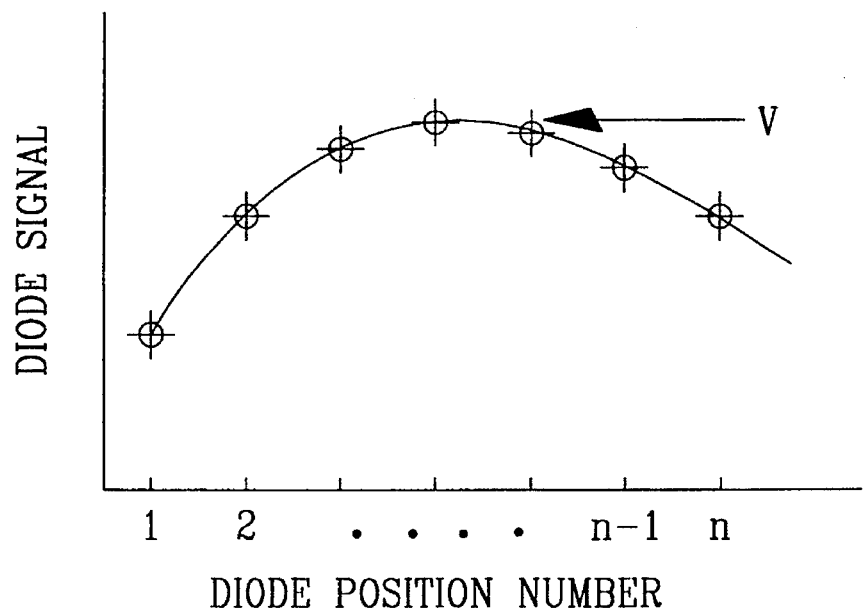
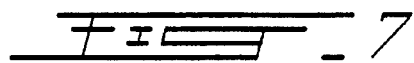

METHOD AND APPARATUS FOR ON-LINE MEASUREMENT OF PULP FIBER SURFACE DEVELOPMENT

BACKGROUND OF THE INVENTION

1) Field of Invention

This invention relates to a method and an apparatus for the on-line determination of the degree of fiber surface development of pulp during stock preparation by refining or beating (the term 'refining' henceforth will be used to denote both 'refining' and 'beating').

2) Description of the Prior Art

Refining is one of the most important stages of stock preparation in paper making. It provides the finished paper with such specific properties as strength, tear, bulk, bonding, rigidity, opacity, formation etc. It also influences the drainage characteristics of the pulp stock and consequently affects the sheet-making operation on the paper machine.

Refining is applied to the production of both mechanical and chemical pulps but in rather different ways. In mechanical pulping, refining is an integral part of the pulping process since it is employed to convert the wood directly into fibers. In chemical pulping, refining is a secondary operation. The fibers are first separated by cooking the wood chips with chemicals and are then subsequently refined. The action of refining produces increased external and internal fibrillation, and fiber shortening. It is these phenomena which lead to the improvement of the finished paper properties.

Historically, the degree of refining of both mechanical and chemical pulps has been monitored by means of freeness measurements applied to samples withdrawn from the process. The freeness test is essentially a drainage test; it is normally performed with the Canadian Standard Freeness (or the Schopper-Riegler) tester. This test was originally developed on an empirical basis, and although it has therefore been frequently criticized for this reason, it has been maintained as a standard over many years because it is simple to operate and provides a measurement rapidly.

In recent times, a number of on-line drainage devices have been developed to replace the off-line freshness test in order to provide an automated measurement and hence improved process control. Such instruments as the Bolton-Emmerson Drainac, the Innomatic, the Koei Newfreenester, the Kajaani PDA (Pulp Drainage Analyzer), the Bonnier DRT (Drainage Rate Transmitter), and the Sunds PQM (Pulp Quality Monitor) have been introduced. These devices, while providing improved process control, do not generally produce measurements which directly represent freeness. Furthermore, in the operation of these devices, there is invariably a need for the measurement or control of the consistency of the stock.

Since the empirical character of the freeness and drainage measurements make them unsatisfactory as standards, many researchers have attempted to provide an alternative, more comprehensive characterization of pulp in terms of other, fundamental properties. For example, Clark (Tappi 45(8): 628 (1962) proposed fiber length, coarseness, cohesiveness, intrinsic strength and wet compactibility; Bridge and Hammer (Paper Tech Ind 18(12): 37 (1977) suggested fiber length, coarseness, intrinsic strength, fiber length distribution, specific surface area, and area bonding potential. Forgacs (PPMC 64(C): T89 (1963), in his attempts to characterize groundwood, proposed two properties alone, L factor, related to fiber length, and S factor, related to the specific surface of the 48–100 mesh screen fraction. Additional properties suggested by other researchers have included other forms of fiber length, fiber size distribution, specific volume, cell wall thickness, flexibility, compressibility, fiber/fines ratio, shive content and water retention among others. Clearly, many of these are inter-related.

To reduce the number of the preceding fiber properties to a minimum that may be considered as the basic parameters, there are three which have been identified as occurring the most frequently, by Casey (Pulp and Paper, 3rd. Ed, Vol. 2, p. 839 (1980)) for example, and which appear best to satisfy the criteria.

These are:

fiber length; in refining, the fiber length is subject to reduction by refiner cutting action fiber specific surface; in refining, the specific surface is modified by external fibrillation or fiber splitting flexibility; in refining, the flexibility is modified by internal fibrillation or bruising.

The manner in which, and by what amount, each of these properties contribute to the freeness is difficult to delineate specifically since the results from using different pulp types and different refining processes are not the same. However, the measurement of the specific surface area, which would indicate the increase in fiber surface development during refining, would provide the most direct index of the quality of refining. The measurement of the external specific surface area of pulp fibers has been performed by diverse techniques which include microscopic, fiber silvering and nitrogen adsorption measurements. However, it has been more generally obtained from drainage measurements of the type described by Ingmanson (Tappi 35(10): 439(1952), Parker and Mih (Tappi 47(5): 254(1964), Kerstin Olander, (Tappi 81(1991), Hammer (Paper Tech 15(5): 263(1974), and by Robertson and Mason (PPMC 50(13): 1 (1949). The permeability method of Robertson and Mason provides the means that is most commonly used; this approach has been implemented commercially through the introduction of the Pulmac Permeability Tester.

In addition to drainage methods, optical methods have also been proposed for the measurement of specific surface or similar surface development characterizations.

Mason (Tappi 33(8): 403(1950)), described a laboratory technique in which the transmission of light through a pulp suspension was attenuated by changes in fiber specific surface and other pulp properties. This approach required a measure of consistency.

Silvy and Pascal (ATIP (22): 205(1968)) measured signals from angularly diffracted light from a beam transmitted through a pulp suspension; the ratio of these signals provided an index of the degree of refining.

Pettersson, Fladda and Lundquist (patent Sweden 7706320 (Dec. 27, 1987)) described a method for the measurement of the size distribution of solids in a flowing suspension. This was effected by the detection of light transmitted through the suspension, and by a combination of the separate AC and DC components of the signal.

Pettersson and Karlsson (patent U.S. Pat. No. 4,529,309 (Jul. 16, 1985)) determined the average radius and/or the average length of particles carried by a flowing medium. In this case, signals were obtained from two detectors measuring radiation through a particle suspension, and the AC component from one was combined with the DC component of the other.

Forgacs and Karnis (Canadian Patent 938128 Dec. 11, 1973)), Forgacs and Karnis (U.S. Pat. 3,802,964 (Apr. 9, 1974)), Karnis and Wood (U.S. Pat. No. 4,135,389 Jan. 23, 1979)), Karnis and Shallhorn (U.S. Pat. No. 4,276,119 (Jun.

30, 1981)), Karnis (Canadian patent 1,123,626 (May 18, 1982)), and Karnis and Shallhorn U.S. Pat. No. 4,441,960 (Apr. 10, 1984) determined the specific surface of pulp fibers from turbidity measurements at known consistencies.

Simms and Madson (U.S. Pat. No. 4,159,639 (Jul. 3, 1979)) described an optical method for measuring the degree of refining by monitoring the rate of descent of a pulp-water interface of a pulp suspension at a selected consistency.

Shimuzu, Usuda and Kadoya (Japan Tappi 35(7)): 609(1981)), compared the intensity of signals of light transmitted directly through a pulp suspension and light scattered at an angle to the forward axis, and related a combined signal to the degree of beating of the pulp.

Fedko, Dorf and Slavutskii (patent SU 1075123 (Feb. 23, 1984)) described the measurement of specific surface by light scattering of particles as they settle in a column of liquid.

Unger, Heinemann, Trankner and Strassberg in patent DD 218463 (Feb. 6, 1985) and the paper, "Comparative examination of different methods for determining specific surface of pulp fibers in suspension", Zellstoff Papier 32, no 4: 154:157 (July/August 1983)) described an invention which uses turbidity measurements to determine light scattering and hence specific surface.

Bott (U.S. Pat. No. 4,676,641 (Jun. 30, 1987)), described a goniometric technique for measuring light scattering, principally of very small particles in suspension, and related these measurements to the particle size distribution.

Most of these methods require an accurate consistency measurement of the pulp stock.

Meyn, Landmark and Aagedal (J. Institute of Measurement and Control 1(9); T165(1968) described an optical method for measuring pulp consistency. This employs a combination of signals from polarized light beams transmitted through pulp stock, one beam with its plane of polarization in line with that of the incident beam, the second with its plane of polarization at ninety degrees.

Two commercial instruments, the EUR-Control Lowcon and the Kajaani LC-100 were designed using this principle of operation. Simms and Madson (U.S. Pat. No. 4,171,916 (Oct. 23, 1979)) described a method which is also based on the same principle of operation.

Saltzman (U.S. Pat. No. 3,283,644 (Nov. 8, 1966)) at an earlier date described the same method applied to the measurement of concentrations of solids in suspensions.

Leschonski (patent DE 3105752 (Jan 17, 1981)) measured forward scattered light by light extinction and gamma (or similar) radiation to determine concentration.

SUMMARY OF THE INVENTION

It is an object of this invention is to provide a novel apparatus for measuring the degree of fiber surface development of pulp during refining without the requirement of an accompanying consistency measurement.

It is a further object of this invention to provide a novel method for determining the degree of fiber surface development in a stock of fibrous pulp, without a requirement of an accompanying consistency measurement.

It is a still further object of this invention to provide an improvement in apparatus for determining the degree of refining of a stock of fibrous pulp In accordance with one aspect of the invention there is provided an apparatus for determining the degree of fiber surface development in a stock of fibrous pulp comprising: i) a sample flow passage adapted to connect with a source of developing fiber pulp, for flow of a sample of stock of fibrous pulp from the source, ii) flow means to convey a sample of stock of fibrous pulp from the source, along said flow passage, iii) an optical cell having an optical path for light transmission, said flow passage intersecting said optical path, iv) said flow passage having an entry window and an opposed exit window for transmission of light along said optical path and across said-flow passage, said entry and exit windows being non-light polarizing, v) means to establish a gradual variation in a single mode in the mass of fibers in the sample, at the intersection of the sample flow path and the optical path, vi) means in said cell to develop a beam of polarized light with a first plane of polarization, adjacent to said entry window, in said optical path, vii) polarizing filter adjacent to said exit window, in said optical path, adapted to pass light transmitted through said flow passage and exit window, along a second plane of polarization perpendicular to said first plane, viii) detection means to measure the intensity of transmitted light in said optical path at exit of said polarizing filter and identify a peak light transmission for the sample, as a measure of the degree of fiber surface development in the sample.

In accordance with another aspect of the invention there is provided a method of determining the degree of fiber surface development in a stock of fibrous pulp comprising a) providing a sample flow path and an optical path intersecting said sample flow path, b) conveying a sample of a stock of fibrous pulp along said sample flow path, c) establishing a gradual variation in the mass of fibers at the intersection of said sample flow path and said optical path, while transmitting polarized light having a first plane of polarization through said stock, along said optical path, said gradual variation being in a single mode, d) passing the light exiting said stock in said optical path along a second plane of polarization perpendicular to said first plane, e) measuring the intensity of the transmitted light from d), and f) determining the peak light transmission for the sample as a measure of the degree of fiber surface development.

In accordance with still another aspect of the invention there is provided an apparatus for determining the degree of refining of a stock of fibrous pulp having means to withdraw a sample of the stock and means to measure a parameter of the stock in the sample, as a measure of the degree of refining, the improvement wherein the means to measure a parameter of the stock comprises: i) an optical cell having an optical path for light transmission, ii) a flow passage defined in said cell, for flow of the sample, said flow passage intersecting said optical path, iii) said flow passage having an entry window and an opposed exit window for transmission of light along said optical path and across said flow passage, said entry and exit windows being non-light polarizing, iv) means in said cell to develop a beam of polarized light with a first plane of polarization, adjacent to or at the entrance to said entry window, in said optical path, v) a polarizing filter adjacent to or at the exit of said exit window, in said optical path to polarize all light transmitted through said flow path and exit window in said optical path, along a second plane of polarization perpendicular to said first plane, vi) detection means to measure the intensity of transmitted light in said optical path downstream of said exit window.

The purpose of the invention is to provide a measure of a property of pulp stock during production which will assist in the prediction and control of the final paper quality.

The method of implementation is by a measurement of surface quality which represents an index of specific surface area. In accordance with the present invention, a sample of refined pulp suspension is withdrawn from the process and passed through an in-line optical test cell in an independent circulating stock line loop. A collimated beam of light is passed through a linear polarizer, transmitted through the pulp suspension circulating through the optical cell, is passed through a second polarizer, and collected by a photodetector. The planes of polarization of the two polarizers are positioned perpendicular to each other.

DESCRIPTION OF PREFERRED EMBODIMENTS

The polarizers are, in particular, either both linear polarizers or both circular polarizers.

In one embodiment the consistency of the sample is progressively decreased by dilution, and this causes a change in the detector signal which gradually increases to a maximum value, then decreases. This maximum value is recorded, and provides an index of the degree of fiber surface development indicating the degree of refining of the pulp.

In this first embodiment the gradual variation in the mass of fibers in a single mode is achieved by gradually diluting the sample to decrease the consistency of the fibrous pulp during the transmission of the polarized light, with the intensity of the light being measured at the different consistencies of the fibrous pulp.

This diluting is suitably conducted in a dilution vessel with diluent being introduced into the vessel via a diluent inlet, to dilute the sample in the vessel; a control valve controls flow of diluent through the diluent inlet to the vessel.

A first sensor sends a signal, responsive to a first predetermined level of dilution in the vessel, to initiate flow of the diluted sample from the dilution vessel to the flow path; the signal activates a control member to permit flow of the sample from the vessel to the flow path.

A second sensor sends a signal, responsive to a second predetermined level of dilution in the vessel to the control member to cease flow of diluted sample to the flow path and also signals a control valve to terminate flow of diluent through the diluent inlet.

The second predetermined level of dilution is higher than the first predetermined level.

In another embodiment the need for changing the consistency of the stock feeding into the cell is avoided, instead the stock is diluted to an approximate predetermined value. In this instance, the optical cell incorporates a stock flow channel which decreases gradually in one direction, and a linear array of detectors inserted alongside the exit wall. The detectors register signals which are generated at varying magnitudes, gradually increasing and then decreasing across the array. The maximum value is identified and recorded; this provides the measurement representing the index of the degree of fiber surface development.

In this latter embodiment the flow path decreases gradually in cross-sectional dimension in one direction thus forming, for example, a channel the walls of which converge in one direction, or a wedge shaped channel. This gradual decrease in cross-sectional dimension occurs in the region of intersection of the flow path and the optical path.

The polarized light is divided into a plurality of parallel, spaced apart discrete beams entering the flow path; and each resultant polarized beam exiting the flow path is exposed on an element of the array of detectors, which is, in particular a linear photodetector array.

It will be understood that references to "entrance" and "exit" refer to locations in the optical path in which the entrance is on the light source side of the cell and the exit is on the detector side of the cell.

It will also be understood that the gradual variation in the mass of fibers being in a "single mode" is intended to indicate a progressive change in one direction by which is meant a progressive increase or, a progressive decrease, as distinct from a variation which fluctuates with increases and decreases.

The polarization effected by the entrance and exit polarizers is such that in the absence of fibers in the flow path, no light would be transmitted by the exit polarizer; but with fibers present in the flow, depolarization would occur and light would be transmitted by the exit polarizer.

BRIEF DESCRIPTION OF THE DRAWINGS

FIG. 6 is a schematic diagram of an alternative design of the pulp quality measuring device, fabricated with converging windows;

FIG. 7 is a graph showing the variation of the optical cell output signal with respect to the diode positions in the linear photodiode array;

DESCRIPTION OF THE PREFERRED EMBODIMENTS WITH REFERENCE TO THE DRAWINGS

Figure 1:
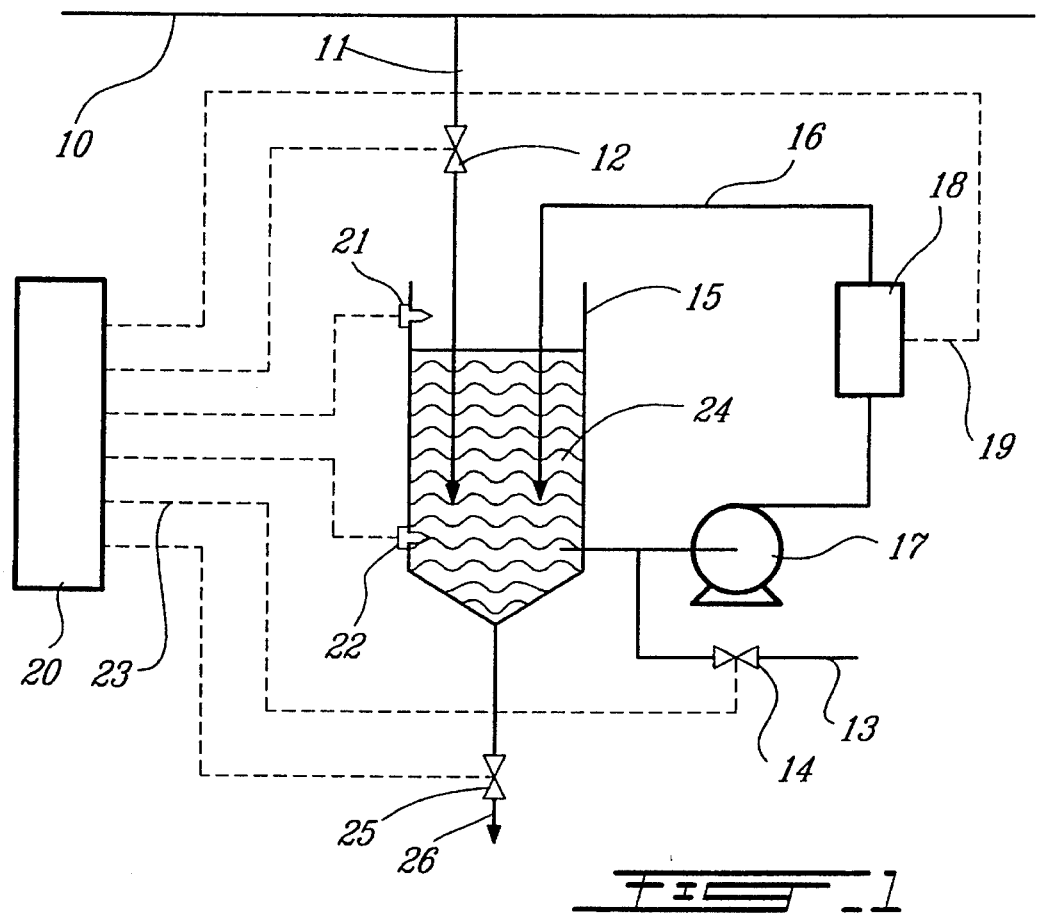
FIG. 1 is a schematic illustration of the stock sampling and pulp quality monitoring system of the present invention.

Referring to FIG. 1, an embodiment of the sampling system and measuring device is shown. A discrete amount of sample of stock is periodically removed from a process main stock line 10 and sent through line 11 to a mixing tank 15. An automatic controller 20 initiates this procedure by operating valve 12 at preset timed intervals. When the valve 12 operates, valve 14 is opened simultaneously to admit dilution water through line 13 to the tank 15 and to the inlet side of a pump 17. After a short interval, the stock surface level reaches a lower level sensor probe 22. At this point, the overall consistency of stock sample 24 in the tank 15 has been diluted to be within a predetermined range of typically between 0.1 and 0.2 percent. When contact is made between the stock 24 and the lower sensor probe 22, the pump 17 is switched on and the stock 24 is circulated through an optical cell 18 in a test line 16. Concurrent with this operation, the output signal from the optical cell unit 18 is fed to a microprocessor data acquisition and control unit 20 and continuously recorded. Mixing of the stock 24 is provided by the action of the pump 17. The dilution water supplied through line 13 and via the pump 17 is gradually added to the stock 24 in the mixing tank 15, causing the overall consistency of the stock sample to be reduced as the sample level surface approaches an upper sensor probe 21. When contact is made between the stock 24 and the upper level probe 21, the pump 17 is switched off, the dilution line valve 14 is closed, and the recording of the control unit output signal 20 stops. An exhaust valve 25 opens allowing the contents of the circulating system to discharge through line 26 into the sewer or back to the process. When the stock has emptied out of the tank 15, a flush cycle is operated and water from line 13 is circulated through the system through line 16 to remove residual pulp. On completion of the flushing operation, the automatic controller 20 starts the next cycle with the removal of a new sample from the main stockline 10.

Figure 2:
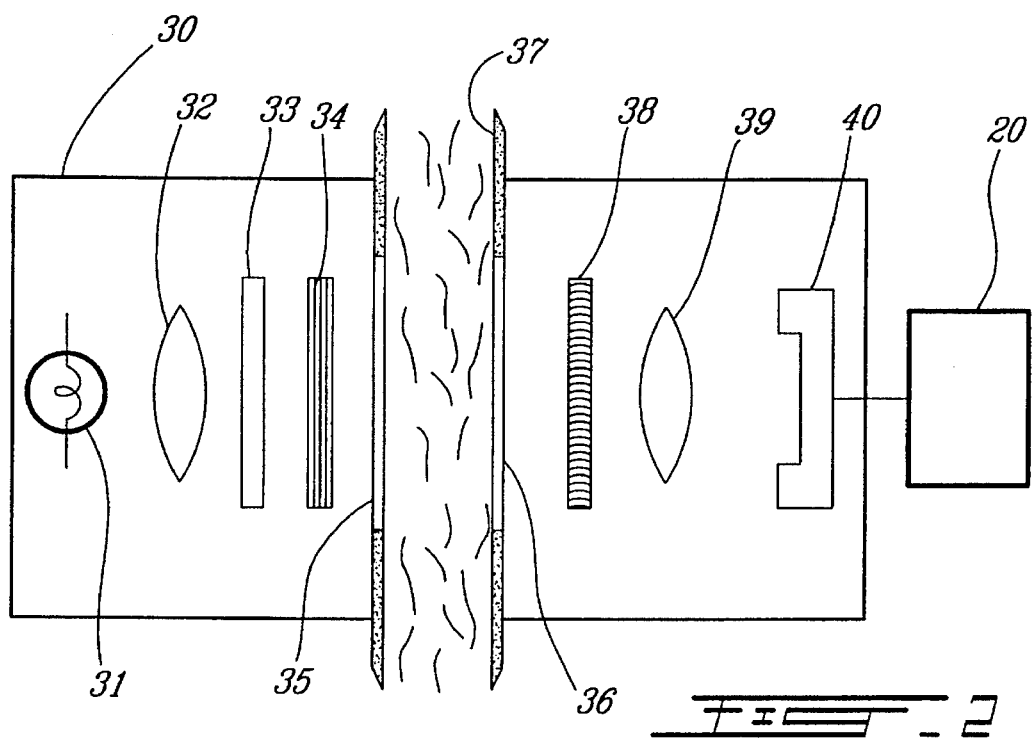
FIG. 2 is a schematic diagram of the optical pulp quality measuring device, fabricated with parallel windows.

Referring to FIG. 2, an optical measuring system for determining the degree of refining of pulp fibers in accordance with the present invention is shown. A radiation source 31 is a tungsten halogen lamp powered from a stabilized voltage supply. The radiation from the lamp 31 is collimated by a convex lens 32, passed through an optical filter 33 and a visible linear or circular polarizing filter 34, and is directed on to an incident window 35 of a stock sample cell 37. The sample cell 37 is constructed with a pair of parallel plane windows 35,36 of suitable optical grade clear glass which exercises no polarizing effect on the light. The cell 37 is typically fabricated with 32 mm (1.25 in) diameter windows, 12.5 mm (0.5 in) apart, designed for installation in a 25 mm (1 in) test line 16 in FIG. 1. The light beam emerging from exit window 36 of the cell 37 passes through a second visible linear or circular, respectively, polarizing filter 38. This filter 38 is installed with its polarizing plane rotated through 90 degrees, or with the opposite circularity, with respect to that of the first filter 34. The beam is passed through a second convex lens 39, and focused onto a photodetector 40 which registers the intensity of the transmitted beam with the microprocessor data acquisition unit 20.

Figure 3:
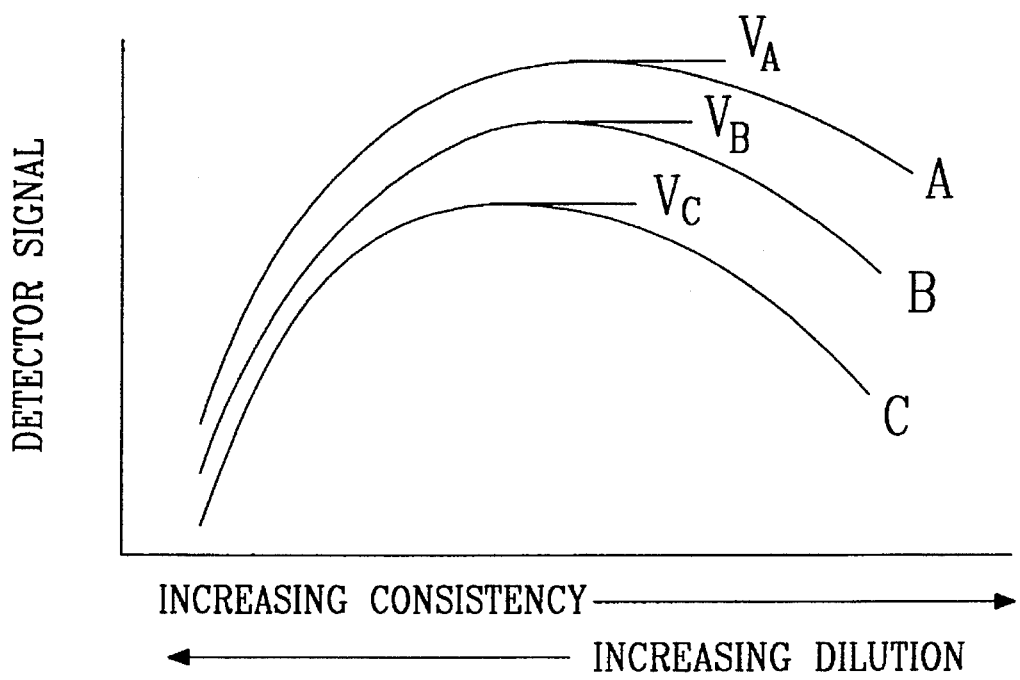
FIG. 3 is a graph showing the variation of the optical cell output signal during stock dilution, for three samples of pulp refined to different degrees.

Referring to FIG. 3, each of the curves in the graph represents a plot of the photodetector output signal against the sample consistency during the dilution cycle. The signal increases with the initial dilution, and then, as the dilution continues, the rate of increase reduces. The signal increase continues until it reaches a maximum value, reverses direction and falls away. The three individual curves represent pulp samples from a common supply subjected to different degrees of refining. The curve A represents the sample which has been refined with the least amount of specific energy, and produces the highest freeness value. The curve B represents a sample refined with more energy resulting in lower freeness. The curve C represents the sample refined with the greatest amount of specific energy, resulting in the lowest freeness. From these curves, an index of the degree of refining to which the samples have been exposed is indicated by the peak values $V_A$, $V_B$, and $V_C$, i.e. the maxima of their corresponding curves.

Figure 4:
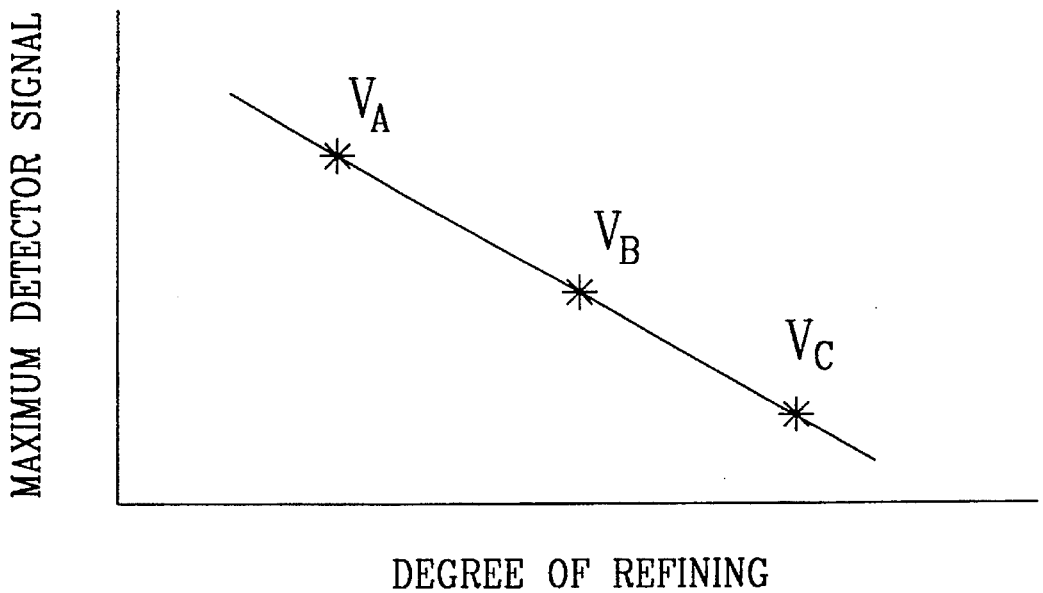
FIG. 4 is a graph showing the relationship between the maxima of the optical cell output signal and the degree of refining of the three samples.

Referring to FIG. 4, the graph represents the plot of the maxima $V_A$, $V_B$, and $V_C$ against the degree of refining; this illustrates how the optical measurement is applied to monitor the refining operation.

The concept of the invention is based on the behavior of plane polarized light when transmitted through pulp stock. The transmitted light comprises the component of the incident light which is displaced through a 90 degree phase change. The intensity of this component is dependent on the concentration of the fibers, and on the fiber surface quality. While the exact principle of this operation has not yet been fully established, it is attributed to two phenomena:

The first is that of the light depolarization. The cellulose fraction of wood pulp fibers contains a crystalline component which is birefringent and therefore a primary cause of change in the plane of polarization of the transmitted light. Some secondary depolarization of the light may be also attributed to the combined effects of refraction, diffraction, and internal and external reflectance at the optical fiber boundaries. As a result of these effects, the intensity of the transmitted, crossed polarization component increases with the concentration of the depolarizing fibers. The result may be represented by the equation $$I_p = I_o (1 - e^{-apC}) \tag{1}$$

where Ip represents the transmitted light intensity (due to the cross-depolarization by the fibers), $I_0$ represents the incident light intensity, p represents a coefficient of depolarization of the pulp fibers, a represents a specific coefficient peculiar to the species and type of pulp, and C represents the concentration of the fibers in the stock.

Figure 5:
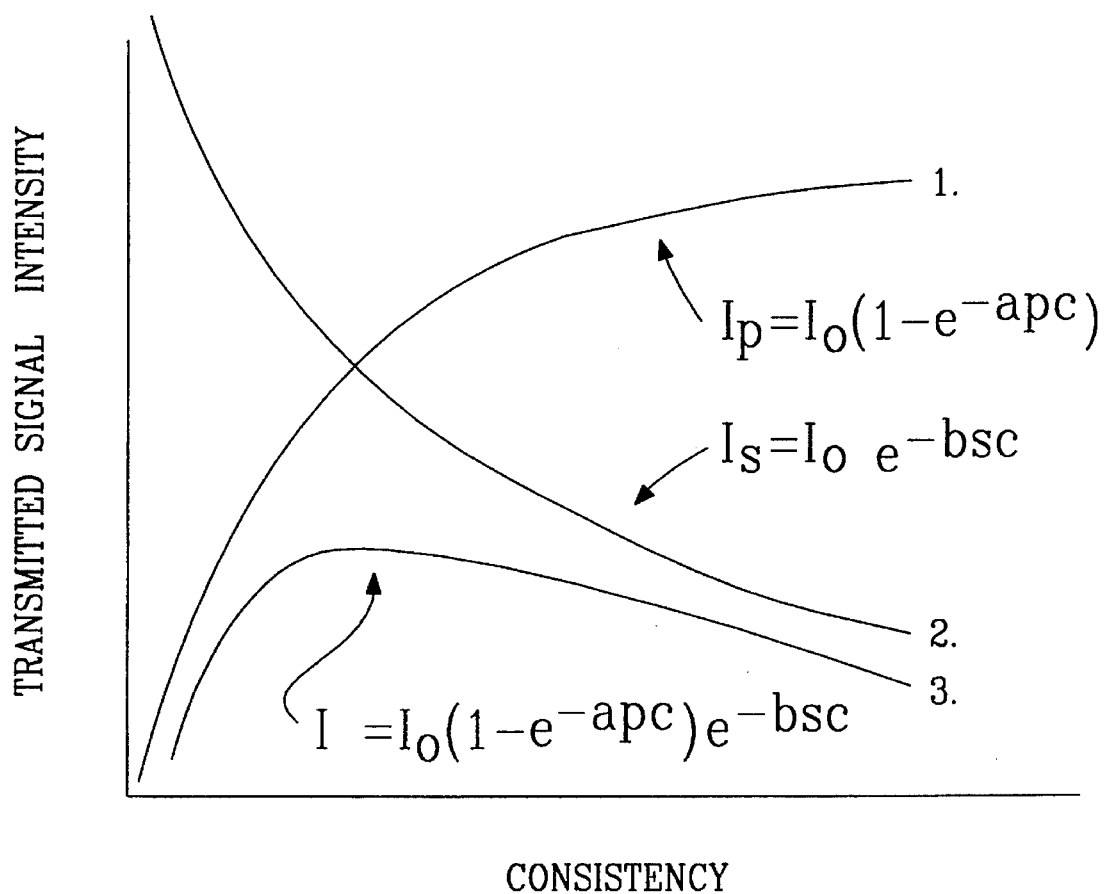
FIG. 5 is a graph representing the derivation of the theoretical relationship between the transmitted light and the concentration of birefringent pulp fibers in a suspension.

Referring to FIG. 5, curve number 1 shows how the transmitted light intensity, as defined above, changes with consistency.

The second phenomenon is that of light scattering. Light scattering is caused by the discontinuities at the optical fiber boundaries. The amount of scattering is determined by the size of the boundaries and the differences between the refractive indices of the fibers and water phases. The relationship between the surface properties of pulp fibers and their light scattering behavior has been described, for example, by Mason (Tappi 33(8): 403(1950)). The form of the relationship is analogous to that provided by the Beer-Lambert law for the attenuation of transmitted light and may be represented by the equation $$I_s = I_o e^{-bsC} \tag{2}$$

p where $I_s$ represents the transmitted light intensity due to the light scattering of the fibers, $I_o$ represents the incident light intensity, b represents a coefficient peculiar to the species and type of pulp, s represent the coefficient of light scattering by the fibers, and C represents the concentration of the fibers in the stock.

Referring to FIG. 5, curve number 2 shows how the transmitted light intensity, as defined above, changes with consistency.

When the two phenomena are present simultaneously, their effects are multiplative so that the resulting signal can then be represented by the equation $$I = I_o (1 - e^{-apC}) e^{-bsC} \tag{3}$$

where I represents the overall transmitted light intensity.

Referring to FIG. 5, curve number 3 therefore represents the manner in which the overall transmitted light intensity changes with consistency.

The three curves shown in FIG. 3 thus represent variations of the curve shown in FIG. 5, curve number 3 for three degrees of refining. When refining takes place, there is an increase in the pulp fiber surface area which is accompanied by an increase in the light scattering coefficient, s. This causes a decrease in $I_s$ in equation (2), while $I_p$ is assumed to be unchanged. Thus the changes from $V_A$ to $V_B$ to $V_C$ in FIG. 3 occur as a result of the decrease of s in the combined equation for I in equation (3).

In the foregoing analysis, no provision is made for any effects due to light absorption. It is believed that by using an optical filter 33, shown in FIG. 2, which is selected to operate in a red/near-infrared wavelength band, the light absorption coefficient of the pulp may be considered to be negligible.

Other methods for varying the consistency or effective path length are possible. Referring to Fig. 6, one embodiment of an alternative optical measuring system for determining the degree of refining of pulp fibers in accordance with the invention is shown. The apparatus is mounted within a light-tight housing. The radiation source 51 is a tungsten halogen lamp powered from a stabilized voltage supply. The radiation from the lamp 51 is collimated by a convex lens 52, passed through an optical filter 53, a visible linear polarizing filter 54, and through a slotted mask 55 which transforms the primary beam into a set of discrete narrow parallel beams directed on to incident window 56 of stock sample cell 58. The cell 58 is designed in the form of a converging channel such that the mass of fibers presented to the light beams reduces progressively along the length of the cell. The cell 58 is fabricated with a pair of clear glass rectangular windows 56, 57 which exercise no polarizing effect on the light. The set of light beams emerging from the exit window 57 of the cell passes through a second visible polarizing filter 59. This filter is positioned with its polarizing plane rotated through 90 degrees with respect to that of the first filter 54. A linear photodetector array 60 is installed alongside the exit polarizer 59, and across the emerging beams. Each element of the photodetector array is exposed to the light transmitted through the slotted segment of the cell 58 adjacent to it. An alternative method would have individual segments illuminated sequentially.

Referring to FIG. 7, the curve in the graph represents a plot of the responses of the individual detectors traversing the array. The signals first exhibit increasing intensity corresponding to increasing amounts of fiber in the segments adjacent to the detectors; the signals approach maximum value, and then decreasing values with the further increases in segment fiber mass. In this manner, the operation of the converging window optical cell is similar to that of the original, parallel window optical cell. The type of measurement data shown in FIG. 7 is comparable with that shown in FIG. 3, and the maxima signal data from it may be processed in the same way as indicated in FIG. 4. The converging window cell is designed to accommodate the passage of stock flowing through continuously, as opposed to the intermittent sampling strategy used for which the parallel window cell design of FIG. 2 is employed. The specified requirement for its operation is that the consistency must be controlled to within a specific, narrow range of values. Typically the consistency will be 0.10% +/-0.01% for a cell of width 12.5 mm (0.5 in) at the center.

It will be appreciated that the two cell designs as described above constitute alternative means of achieving the same result, that is to vary the mass of the fibers in the optical path in the test cell. Accordingly, it is possible to achieve this goal by using other geometrical arrangements in the optical cell design.

EXAMPLE

Samples from three different types of pulps, a bleached softwood kraft, a softwood sulphite and a refiner mechanical pulp, refined to different degrees of freeness, were circulated through an optical cell in a test unit, incorporating a Newport Model 780 lamp system and an Oriel Model 71821 integrated photodiode-amplifier unit, as illustrated in FIG. 2. The sensor output measurements, representing the peak transmitted light intensity values, were obtained and recorded for each of the samples.

| i) Bleached softwood kraft | | ii) Softwood sulphite | | iii) RMP | |
| --- | --- | --- | --- | --- | --- |
| Freeness mL CSF | Signal $V_{MAX}$, mV. | Freeness mL CSF | Signal $V_{MAX}$, mV. | Freeness mL CSF | Signal $V_{MAX}$, mV. |
| 614 | 171.4 | 546 | 167.8 | 345 | 54.75 |
| 596 | 171.0 | 501 | 165.7 | 331 | 54.72 |
| 512 | 170.1 | 447 | 163.3 | 336 | 54.75 |
| 414 | 167.8 | 386 | 159.5 | 293 | 54.45 |
| 328 | 164.4 | 336 | 157.0 | 258 | 53.95 |
| 259 | 160.0 | 245 | 153.2 | 211 | 52.50 |
| 200 | 156.7 | 192 | 150.1 | 183 | 51.85 |
| 147 | 151.8 | 155 | 145.9 | 156 | 50.50 |

Figure 8:
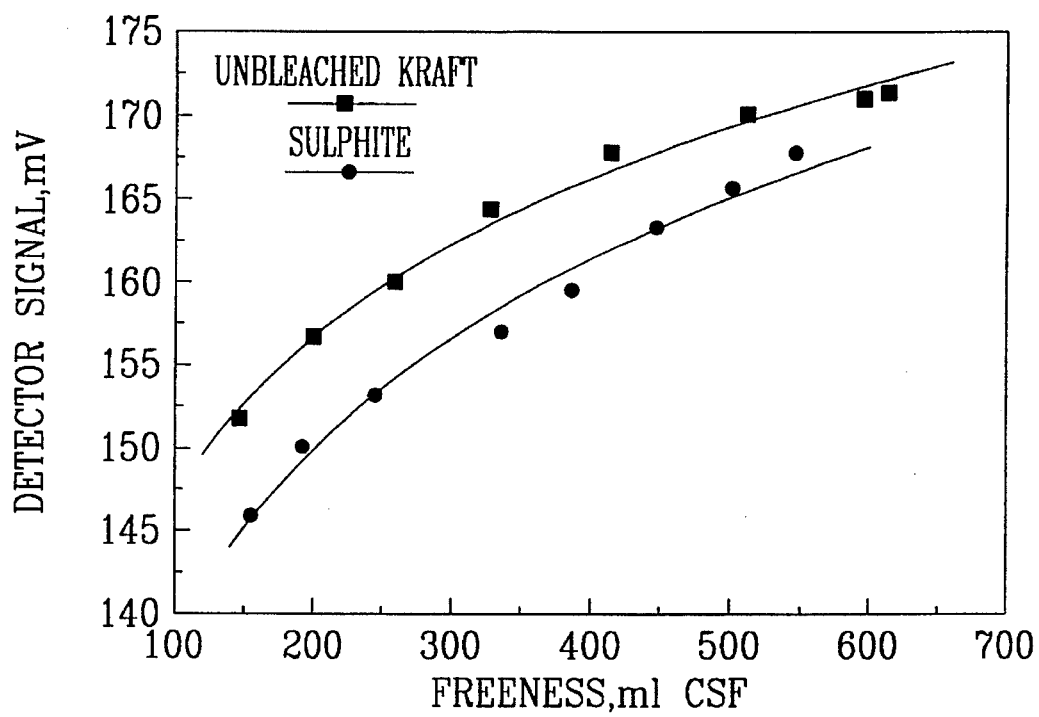
FIG. 8 is a graph showing the variation of the optical cell output signal with the freeness of refined unbleached and sulphite pulp samples.
Figure 9:
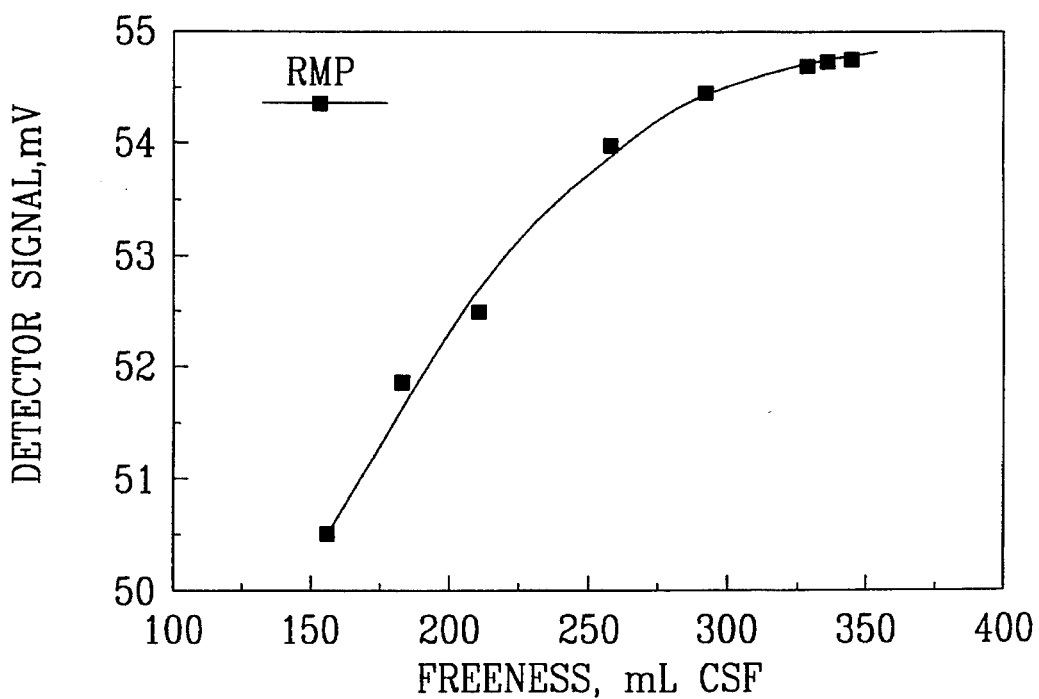
FIG. 9 is a graph showing the variation of the optical cell output signal with the freeness of RMP samples.

The relationships between the detector output and corresponding freeness measurements representing the degree of refining are shown in FIG. 8 for the two chemical pulps and in FIG. 9 for RMP. These results explicitly demonstrate a high degree of correlation between the two variables which indicates the viability of the sensor for monitoring pulp refining.

What is claimed is:

1. A method of determining the degree of refining in a stock of fibrous pulp comprising:

i) determining a peak light transmission for each of plurality of pulp samples subjected to different known degrees of refining and establishing a relationship between peak light transmission and degree of pulp refining;

ii) a) providing a sample flow path and an optical path intersecting said sample flow path, b) conveying a sample of a stock of fibrous pulp along said sample flow path, c) establishing a gradual variation, by progressive increase or progressive decrease, in the mass of fibers at the intersection of said sample flow path and said optical path, while transmitting polarized light having a first plane of polarization through said stock, along said optical path, d) polarizing the light exiting said stock in said optical path along a second plane of polarization perpendicular to said first plane, e) measuring the intensities of the transmitted light from d), during conveyance of said sample along said sample flow path, at different masses of the fibers in step c), and f) determining the peak light transmission for the sample from the measurements in step e), and iii) determining the degree of refining of said stock by comparison of said peak light transmission in step ii) f) and said relationship in step i).

2. A method according to claim 1, wherein said polarized light in c) is linear polarized light and said polarizing in d) is linear polarizing.

3. A method according to claim 2, wherein said flow path decreases gradually in cross-sectional dimension, in one direction, along the intersection with said optical path; in step c ) the polarized light is transmitted through said stock, in said optical path, along a plurality of spaced apart pathways and step e) comprises measuring the intensities of the transmitted light from d) in each pathway.

4. A process according to claim 1, wherein the establishing of the gradual variation is by progressive increase in the mass of fibers.

5. A method accord to claim 1 wherein said determining in step i) comprises subjecting each of said plurality of pulp samples of step i) to steps a) to f) of step ii), said pulp samples in step i) being of a known degree of refining, and establishing a plot relationship between peak light transmission of each of said samples and degree of refining of each of said samples.

6. A method according to claim 5 wherein said plurality of pulp samples of step i) is selected to include samples having a high degree of refining, a low degree of refining and an intermediate degree of refining.

7. A method of determining the degree of fiber surface development in a stock of fibrous pulp comprising:
   a) providing a sample flow path and an optical path intersecting said sample flow path,
   b) conveying a sample of a stock of fibrous pulp along said sample flow path,
   c) establishing gradual variation by progressive increase or progressive decrease, in the mass of fibers at the intersection of said sample flow path and said optical path, while transmitting linear polarized light having a first plane of polarization through said stock, along said optical path,
   d) linear polarizing the light exiting said stock in said optical path along a second plane of polarization perpendicular to said first plane,
   e) measuring the intensities of the transmitted light from d), during conveyance of said sample along said sample flow path, and
   f) determining the peak light transmission for the sample as a measure of the degree of fiber surface development,
   wherein the establishing of the gradual variation by progressive decrease of the mass of fibers in step c), comprises gradually diluting said sample to decrease the consistency of the fibrous pulp in the sample during the transmission of the polarized light, and step e) comprises measuring the intensities of the transmitted light at different consistencies of the fibrous pulp.

8. A method according to claim 7, wherein said diluting is conducted in a dilution vessel and step c) includes introducing diluent into said vessel to dilute said sample, initiating flow of diluted sample from said vessel to said flow path responsive to a first signal indicating a first predetermined level of dilution and terminating flow of diluted sample from said vessel to said flow path responsive to a second signal indicating a second predetermined level of dilution, said second level being a higher level of dilution than said first level.

9. An apparatus for determining the degree of refining in a stock of fibrous pulp comprising:
   i) a sample flow passage adapted to connect with a source of developing fiber pulp, for flow of a Sample stock of fibrous pulp from the source,
   flow means to convey a sample of stock of fibrous pulp from the source, along said flow passage,
   iii) an optical cell having an optical path for light transmission., said flow passage intersecting said optical path, iv) said flow passage having an entry window and opposed exit window for transmission of light along said optical path and across said flow passage, said entry and exit windows being non,light polarizing,
   vi) means to establish a gradual variation, by progressive increase or progressive decrease, in the mass of fibers in the sample, at the intersection of the sample flow path and the optical path,
   vi) means in said cell to develop a beam of polarized light with a first plane of polarization, adjacent to said entry window, in said optical path,
   vii) a polarizing filter adjacent to said exit window, in said optical path, adapted to polarize all the light transmitted through said flow passage and exit window, along a second plane of polarization perpendicular to said first plane,
   viii) detection means to measure the intensities of transmitted light in said optical path at exit of said polarizing filter, during conveyance of the sample along said flow passage and identify a peak light transmission for the sample, from the measured intensities,
   wherein said flow passage decreases gradually in cross-sectional dimension, in one direction along the intersection with said optical path,
   means in said optical path on entrance side of said flow passage to divide the polarized light into a plurality of parallel, spaced apart discrete beams, said polarizing filter vii) being effective to polarize each discrete beam, and
   said detection means comprising a linear photodetector array disposed such that each discrete polarized beam is exposed on a photodetector element of said array.

10. An apparatus according to claim 9, wherein said means v) comprises a dilution vessel in flow communication with said flow passage,
   said vessel having a diluent inlet for introduction of diluent into said vessel,
   a control valve for controlling flow of diluent through said diluent inlet,
   first and second sensors responding to first and second predetermined levels of dilution in said dilution vessel,
   control means responsive to a signal from said first sensor to activate said flow means ii) to permit flow of the sample from said vessel to said flow passage;
   said control means being responsive to a signal from said second sensor to deactivate said flow means ii) to cease flow of the sample from said vessel to said flow passage, and to close the control valve to cease flow of diluent through said diluent inlet.

11. An apparatus according to claim 10, wherein said means vi) comprises a linear polarizer and said polarizing means vii) comprises a linear polarizer.

12. An apparatus according to claim 11, wherein said flow passage is in a flow loop connected with said diluent vessel.

13. An apparatus according to claim 9, wherein said means vi) comprises a linear polarizer and said polarizing means vii) comprises a linear polarizer.

14. In an apparatus for determining the degree of refining of a stock of fibrous pulp having means to withdraw a sample of the stock and means to measure a parameter of the stock in the sample, as a measure of the degree of refining, the improvement wherein the means to measure a parameter of the stock comprises:
   i) an optical cell having an optical path for light transmission,
   ii) a flow passage defined in said cell, for flow of the Sample, said flow passage intersecting said optical path, iii) said flow passage having an entry window and an opposed exit window for transmission of light along said optical path and across said flow passage, said entry and exit windows being non-light polarizing, iv) means in said cell to develop a beam of polarized light a first plane of polarization, at the entrance to said entry window in said optical path, v) a polarizing filter adjacent to said exit window, in said optical path as sole exit polarizer to polarize all light transmitted through said flow path and exit window in said optical path, along a second plane of polarization perpendicular to said first plane, vi) detection means to measure the intensity of transmitted light in said optical path downstream of said exit window and provide a plurality of measured intensities of transmitted light, and vii) means to determine a peak light transmission among said measured intensities of transmitted light, for the sample, as a measure of the degree of fiber surface development in the sample, wherein said flow passage decreases gradually in cross-sectional dimension, in one direction along the intersection with said optical path, means to divide the beam of polarized light into a plurality of parallel, spaced apart discrete beams, said polarizing filter v) being effective to polarize each discrete beam, and said detection means comprising a linear photodetector array, disposed such that each discrete beam is exposed on a photodetector element of said array.

15. An optical cell for use in determining the degree of fiber surface development in a stock of fibrous pulp comprising:

i) an optical cell housing having an optical path for light transmission, ii) a flow passage defined in said cell for flow of a sample stock, said flow passage intersecting said optical path, and decreasing gradually in cross-sectional dimension, in one direction along the intersection with said optical path, iii) said flow passage having an entry window and an opposed exit window for transmission of light along said optical path and across said flow passage, said entry and exit windows being non-light polarizing, iv) means in said cell to develop a beam of polarized light with a first plane of polarization, adjacent to said entry window, in said optical path, v) means in said optical path to divide the beam of polarized light into a plurality of parallel spaced apart discrete beams upstream of said flow passage, vi) polarizing means adjacent to said flow passage, in said optical path to polarize the discrete beams along a second plane of polarization perpendicular to said first plane, and vii) detection means to measure the intensity of each transmitted polarized beam.

16. A method of determining the degree of refining in a stock of fibrous pulp comprising:

i) determining a peak light transmission for each of a plurality of pulp samples subjected to different known degrees of refining and establishing a relationship between peak light transmission and degree of pulp refining;

ii) a) providing a sample flow path and an optical path intersecting said sample flow path, b) conveying a sample of a stock of fibrous pulp along said sample flow path, c) gradually diluting said sample to decrease the consistency of the fibrous pulp in the sample at the intersection of said sample flow path and said optical path, while transmitting polarized light having a first polarization orientation through said stock, along said optical path, d) polarizing the light exiting said Stock in said optical path along a second polarization orientation opposite to said first orientation, e) measuring the intensities of the transmitted light from d) at different consistencies of the fibrous pulp in step c), and f) determining the peak light transmission for the sample from the measurements in step e), and iii) determining the degree refining of said stock by comparison of said peak light transmission in step ii) f) and said relationship in step i).

17. A process according to claim 16, wherein said polarized light in step c) is circularly polarized light and said polarizing in step d) is circular polarizing.

* * * * *